United States Patent
Ghosh et al.

(10) Patent No.: US 12,201,843 B2
(45) Date of Patent: Jan. 21, 2025

(54) SYNCHRONIZING EXTERNAL ELECTRICAL ACTIVITY

(71) Applicant: Medtronic, Inc., Minneapolis, MN (US)

(72) Inventors: Subham Ghosh, Blaine, MN (US); Jeffrey M. Gillberg, Coon Rapids, MN (US); Trent M. Fischer, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 560 days.

(21) Appl. No.: 17/031,201

(22) Filed: Sep. 24, 2020

(65) Prior Publication Data
US 2021/0106832 A1 Apr. 15, 2021

Related U.S. Application Data

(60) Provisional application No. 62/913,030, filed on Oct. 9, 2019.

(51) Int. Cl.
*A61B 5/00* (2006.01)
*A61B 5/021* (2006.01)
(Continued)

(52) U.S. Cl.
CPC .......... *A61N 1/36585* (2013.01); *A61B 5/021* (2013.01); *A61B 5/026* (2013.01);
(Continued)

(58) Field of Classification Search
CPC ............ A61N 1/36585; A61N 1/37247; A61N 1/362–3625; A61N 1/3702;
(Continued)

(56) References Cited

U.S. PATENT DOCUMENTS 4,233,987 A 11/1980 Feingold
4,374,382 A 2/1983 Markowitz
(Continued)

FOREIGN PATENT DOCUMENTS

CN 1043621 A 7/1990
CN 1253761 A 5/2000
(Continued)

OTHER PUBLICATIONS

International Search Report and Written Opinion from PCT Application No. PCT/US2020/053794 dated Feb. 15, 2021, 11 pages.
(Continued)

*Primary Examiner* — Scott M. Getzow
(74) *Attorney, Agent, or Firm* — Mueting Raasch Group

(57) ABSTRACT

Systems and methods are described herein for use in synchronizing electrical activity monitored by a plurality of external electrodes with supplemental cardiac data for use in evaluating a patient's cardiac condition and configuring cardiac therapy. The supplemental cardiac data may include one or more markers indicative of the occurrence of cardiac events and/or data representative of representative of at least one of cardiac electrical signals, cardiac sounds, cardiac pressures, blood flow, and an estimated instantaneous flow waveform provided by a left ventricular assist device.

21 Claims, 10 Drawing Sheets

(51) Int. Cl.
    *A61B 5/026* (2006.01)
    *A61B 5/282* (2021.01)
    *A61B 5/339* (2021.01)
    *A61N 1/365* (2006.01)
    *A61N 1/37* (2006.01)
    *A61N 1/39* (2006.01)

(52) U.S. Cl.
    CPC .............. *A61B 5/282* (2021.01); *A61B 5/339* (2021.01); *A61B 5/686* (2013.01); *A61B 5/7475* (2013.01); *A61N 1/3702* (2013.01); *A61N 1/39622* (2017.08); *A61B 2562/0247* (2013.01)

(58) Field of Classification Search
    CPC .... A61N 1/39622; A61B 5/021; A61B 5/026; A61B 5/282; A61B 5/339; A61B 5/346–366; A61B 5/686; A61B 5/7475; A61B 2562/0247
    See application file for complete search history.

(56) References Cited

U.S. PATENT DOCUMENTS

| | | |
|---|---|---|
| 4,402,323 A | 9/1983 | White |
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,535,763 B1 * | 3/2003 | Hiebert ............. A61N 1/37252 607/32 |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | Van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |

(56) References Cited

U.S. PATENT DOCUMENTS

| | | |
|---|---|---|
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,731,632 B1 | 5/2014 | Zarkh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,861,830 B2 | 10/2014 | Brada et al. |
| 8,948,869 B2 | 2/2015 | Ghosh et al. |
| 8,965,489 B2 | 2/2015 | Ghosh |
| 8,972,228 B2 | 3/2015 | Ghosh et al. |
| 9,031,642 B2 | 5/2015 | Ghosh |
| 9,037,238 B2 | 5/2015 | Stadler et al. |
| 9,119,959 B2 | 9/2015 | Rys et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Ghosh |
| 9,526,435 B2 | 12/2016 | Ghosh |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,603,651 B2 | 3/2017 | Ghosh |
| 9,610,045 B2 | 4/2017 | Du et al. |
| 9,737,223 B2 | 8/2017 | Du et al. |
| 9,750,941 B2 | 9/2017 | Ghosh |
| 9,764,143 B2 | 9/2017 | Ghosh et al. |
| 9,776,009 B2 | 10/2017 | Ghosh et al. |
| 9,782,094 B2 | 10/2017 | Du et al. |
| 9,974,457 B2 | 5/2018 | Ghosh et al. |
| 10,166,396 B2 | 1/2019 | Schrock et al. |
| 10,206,601 B2 | 2/2019 | Gillberg et al. |
| 10,251,555 B2 | 4/2019 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |

(56) References Cited

U.S. PATENT DOCUMENTS

| | | |
|---|---|---|
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0184297 A1 | 7/2011 | Vitali et al. |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1* | 11/2012 | Gosh .............. A61B 5/318 703/2 |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0107507 A1 | 4/2014 | Ghosh et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0148696 A1* | 5/2015 | Lall .............. A61B 5/7217 600/510 |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0022164 A1 | 1/2016 | Brockway et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0059002 A1 | 3/2016 | Grubac et al. |
| 2016/0184590 A1 | 6/2016 | Ghosh |
| 2016/0339248 A1 | 11/2016 | Schrock et al. |
| 2017/0246460 A1 | 8/2017 | Ghosh |
| 2017/0246461 A1 | 8/2017 | Ghosh |
| 2018/0020938 A1 | 1/2018 | Du et al. |
| 2018/0140847 A1 | 5/2018 | Taff et al. |
| 2018/0199843 A1 | 7/2018 | Ghosh et al. |
| 2018/0250514 A1 | 9/2018 | Ghosh |
| 2018/0263522 A1 | 9/2018 | Ghosh et al. |
| 2018/0303840 A1 | 10/2018 | Chopra et al. |
| 2018/0326215 A1 | 11/2018 | Ghosh |
| 2019/0030331 A1 | 1/2019 | Ghosh et al. |
| 2019/0143117 A1 | 5/2019 | Ghosh |
| 2019/0160288 A1 | 5/2019 | Stegemann et al. |
| 2019/0183370 A1 | 6/2019 | Gillberg et al. |
| 2019/0192023 A1 | 6/2019 | Ghosh |
| 2019/0192860 A1 | 6/2019 | Ghosh et al. |
| 2019/0290905 A1 | 9/2019 | Yang et al. |
| 2020/0069949 A1 | 3/2020 | Ghosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 | 2/2005 |
| EP | 2 016 976 | 1/2009 |
| EP | 2 391 270 | 7/2011 |
| EP | 1 925 337 | 3/2012 |
| EP | 2 436 309 A2 | 4/2012 |
| EP | 2 435 132 | 8/2013 |
| WO | WO 1998/026712 | 6/1998 |
| WO | WO 1999/006112 | 2/1999 |
| WO | WO 2000/045700 | 8/2000 |
| WO | WO 2001/067950 | 9/2001 |
| WO | WO 2003/070323 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 | 11/2006 |
| WO | WO 2006/117773 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 | 12/2007 |
| WO | WO 2008/151077 A2 | 12/2008 |
| WO | WO 2006/069215 A3 | 6/2009 |
| WO | WO 2009/079344 | 6/2009 |
| WO | WO 2009/139911 A2 | 11/2009 |
| WO | WO 2009/148429 | 12/2009 |
| WO | WO 2010/019494 | 2/2010 |
| WO | WO 2010/071520 | 6/2010 |
| WO | WO 2010/088040 | 8/2010 |
| WO | WO 2010/088485 | 8/2010 |
| WO | WO 2011/070166 | 6/2011 |
| WO | WO 2011/090622 | 7/2011 |
| WO | WO 2011/099992 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/109618 A2 | 8/2012 |
| WO | WO 2012/110940 | 8/2012 |
| WO | WO 2012/109618 A3 | 11/2012 |
| WO | WO 2012/151364 | 11/2012 |
| WO | WO 2012/151389 | 11/2012 |
| WO | WO 2013/006724 A2 | 1/2013 |
| WO | WO 2013/010165 | 1/2013 |
| WO | WO 2013/010184 | 1/2013 |

(56) References Cited

FOREIGN PATENT DOCUMENTS

| WO | WO 2013/006724 A3 | 4/2013 |
|---|---|---|
| WO | WO 2014/179454 | 11/2014 |
| WO | WO 2014/179459 A2 | 11/2014 |
| WO | WO 2014/179459 A3 | 1/2015 |
| WO | WO 2015/013271 | 1/2015 |
| WO | WO 2015/013493 | 1/2015 |
| WO | WO 2015/013574 | 1/2015 |
| WO | 2019/173599 | 9/2019 |
| WO | WO 2020058314 | 3/2020 |

OTHER PUBLICATIONS

International Search Report and Written Opinion issued May 3, 2012 for International Application No. PCT/US2012/036262; 9 pages.

International Search Report and Written Opinion issued May 3, 2012 for International Application No. PCT/US2012/036302; 9 pages.

International Search Report and Written Opinion issued Aug. 6, 2014 for International Application No. PCT/US2014/036153; 14 pages.

International Search Report and Written Opinion issued Nov. 7, 2014 for International Application No. PCT/US2014/036163; 12 pages.

International Search Report and Written Opinion issued Oct. 28, 2014 for International Application No. PCT/US2014/041928; 15 pages.

International Search Report and Written Opinion issued Oct. 24, 2014 for International Application No. PCT/US2014/041929; 14 pages.

International Search Report and Written Opinion issued on Nov. 4, 2014 for International Application No. PCT/US2014/0247583; 7 pages.

International Search Report and Written Opinion issued on Nov. 12, 2014 for International Application No. PCT/US2014/047971; 7 pages.

International Search Report and Written Opinion issued on Nov. 12, 2014 for International Application No. PCT/US2014/048120; 7 pages.

International Search Report and Written Opinion issued on Mar. 9, 2015 for International Application No. PCT/US2014/069214; 11 pages.

International Search Report and Written Opinion issued on Mar. 17, 2015, for International Application No. PCT/US2014/069192; 11 pages.

International Search Report and Written Opinion issued on Mar. 16, 2015 for International Application No. PCT/US2014/069182; 11 pages.

International Search Report and Written Opinion issued on Apr. 8, 2015 for International Application No. PCT/US2014/069070; 11 pages.

International Search Report and Written Opinion issued on Jun. 11, 2015 for International Application No. PCT/US2015/021442; 13 pages.

International Search Report and Written Opinion issued May 27, 2019 for International Application No. PCT/US2019/023549; 15 pages.

Biffi et al., "Occurrence of Phrenic Nerve Stimulation in Cardiac Resynchronization Therapy Patients: the Role of Left Ventricular Lead Type and Placement Site," Europace, 2013; 15:77-82.

Botker MD, PhD., et al., "Electromechanical Mapping for Detection of Myocardial Viability in Patients with ischemia Cardiomyopathy," Circulation, Mar. 2001; vol. 103, No. 12, pp.

"CardioGuide System Enables Real-Time Navigation of Left Ventricular Leads During Medtronic CRT Implants," Press Release, Apr. 9, 2013, Medtronic, Inc., 2 pgs.

Cuculich, P.S., et al., "The Electrophysiological Cardiac Ventricular Substrate in Patients After Myocardial Infection" J. Am. Coll. Cardiol. 2011; 58:1893-1902.

Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.

Dawoud, F et al., "Inverse Electrocardiogramaging to Assess Electrical Dyssynchrony in Cardiac Resynchronization Therapy Patients," Computing in Cardiology, 2012; 39:993-996.

Freund et al., "A Decision-Theoretic Generalization of Online Learning and an Application to Boosting," *Journal of Computer and System Sciences*, 1997; 55(1):119-139.

Friedman, "Greedy Function Approximation: A Gradient Boosting Machine," *Annals of Statistics*, 2001; 29(5):1189-1232.

Friedman, "Stochastic Gradient Boosting," *Computational Statistics and Data Analysis*, 2002; 38(4):367-378.

Friedman et al., "Additive Logistic Regression: a Statistical View of Boosting," *Annals of Statistics*, 2000; 28(2):337-374.

Fung et al., Chapter 20, Optimization of Cardiac Resynchronization Therapy, Cardiac Resynchronization Therapy, Second Edition, Copyright 2008, Blackwell Publishing Ltd., pp. 356-373.

Ghosh et al. "Accuracy of Quadratic Versus Linear Interpolation in Noninvasive Electrocardiogramaging (ECGI)," *Annuals of Biomedical Engineering*, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.

Ghosh et al. "Application of L1-Norm Regularization to Epicardial Potential Solution of the Inverse Electrocardiogramablem," *Annuals of Biomedical Engineering*, vol. 37, No. 5, May 2009; pp. 902-912.

Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.

"Heart Failure Management" datasheet [online]. Medtronic, Minneapolis, Minnesota, [Last updated on Jun. 3, 2013].Retrieved from the Internet: www.medtronic.com; 9 pages.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Jia et al., "Electrocardiogramaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.

Lumason™, Brochure, Bracco Diagnostocs. Oct. 2014.

Medtronic Vitatron Carelink Encore® Programmer Model 29901 Reference Manual, 2013, Medtronic, Inc., Minneapolis, MN.

Miri et al., "Applicability of body surface potential map in computerized optimization of biventricular pacing," Annals of Biomedical Engineering, vol. 38, No. 3, Mar. 2010, pp. 865-875.

Miri et al., "Comparison of the electrophysiologically based optimization methods with different pacing parameters in patient undergoing resynchronization treatment," 30th Annual International IEEE EMBS Conference, Aug. 2008, pp. 1741-1744.

Miri et al., "Computerized Optimization of Biventricular Pacing Using Body Surface Potential Map," 31st Annual International Conference of the IEEE EMBS, Sep. 2009, pp. 2815-2818.

(56) References Cited

OTHER PUBLICATIONS

Miri et al., "Efficiency of Timing Delays and Electrode Positions in Optimization of Biventricular Pacing: A Simulation Study," IEEE Transactions on Biomedical Engineering, Nov. 2009, pp. 2573-2582.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Nash et al., "An Experimental-Computational Framework for Validating in-vivo ECG Inverse Algorithms," International Journal of Bioelectromagnetism, vol. 2, No. 2, Dec. 31, 2000, 9 pp.

Potse et al., "Mathematical Modeling and Simulation of Ventricular Activation Sequences: Implications for Cardiac Resynchronization Therapy," *J. of Cardiovasc. Trans. Res.*, 2012; 5:146-158.

Prinzen et al., "Cardiac Resynchronization Therapy State-of-the-Art of Current Applications, Guidelines, Ongoing Trials, and Areas of Controversy" *Circulation*, 2013; 128: 2407-2418.

Ridgeway, "The State of Boosting," *Computing Science and Statistics*, 1999; 31:172-181.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.

Silva et al., "Cardiac Resynchronization Therapy in Pediatric Congenital Heart Disease: Insights from Noninvasive Electrocardiogramaging" *Heart Rhythm*, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms: a simulation study," Circulation Research, 1989, 64:449-462.

Strik et al., "Electrical and Mechanical Ventricular Activation During Left Bundle Branch Block and Resynchronization," *J. of Cardiovasc. Trans. Res.*, 2012; 5:117-126.

Svendsen et al., "Computational Models of Cardiac Electrical Activation," Chapter 5, Computational Nov. 2010, pp. 73-88.

Sweeney et al., "Analysis of Ventricular Activation Using Surface Electrocardiograma Predict Left Ventricular Reverse Volumetric Remodeling During Cardiac Resynchronization Therapy," *Circulation*, Feb. 9, 2010; 121(5):626-34. Available online Jan. 25, 2010.

Sweeney et al., QRS Fusion Complex Analysis Using Wave Interference to Predict Reverse Remodeling During Cardiac Resynchronization Therapy, heart Rhythm, 2014, 11:806-813.

Turner et al., "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., Application of the Method of Fundamental Solutions to Potential-based Inverse Electrocardiogramnals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

SYNCHRONIZING EXTERNAL ELECTRICAL ACTIVITY

The present application claims the benefit of U.S. Provisional Application No. 62/913,030, filed Oct. 9, 2019, which is incorporated herein by reference in its entirety.

The disclosure herein relates to systems and methods for use in synchronizing electrical activity monitored by a plurality of external electrodes with supplemental cardiac data for use in evaluating a patient's cardiac condition and configuring cardiac therapy.

Systems for configuring medical devices and evaluating a patient's cardiac condition may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

SUMMARY

The illustrative systems and methods described herein may be configured to assist a user (e.g., a physician) in evaluating and configuring cardiac therapy (e.g., cardiac therapy being performed on a patient during and/or after implantation of cardiac therapy apparatus). In one or more embodiments, the electrode apparatus of the systems and methods may be described as being noninvasive because such electrode apparatus may take electrical measurements noninvasively using, e.g., a plurality of external electrodes attached to the skin of a patient about the patient's torso.

The illustrative systems and methods may be described as being configured to link implantable cardiac device marker data and other data with external sensor instruments or another implantable device. Integrating implantable cardiac device markers with external sensor instruments may have many different applications in enhancing various capabilities for better detection and diagnosis. For example, implantable cardiac devices may include sense amplifiers for detecting intrinsic activities in different chambers of the heart as well as timing markers for delivery of pacing by one or more leads or devices to certain chamber(s) of the heart. Synchronization of the data with an external sensor system and instrument may help in detection and subsequent diagnosis.

For instance, the "ECG belt" is an external surface mapping system comprising multiple external ECG sensors/electrodes positioned on a patient's torso. Knowing the timing of a ventricular pacing event from the device (e.g., left ventricular pacing) may help the external surface mapping system "blank out" or have other ways of eliminating data for a certain time period after pacing (e.g., 5 ms) to eliminate potential artifacts in the external electrical signals. Further, it can also help detect beginning of depolarization (QRS) complexes during ventricular pacing as well as ventricular sensing from the device. Other implantable device data (e.g. pace programming parameters) may be also integrated during recording and/or processing of external sensor (in this case, ECG) data to help annotate the data.

The illustrative systems and methods may be configured to synchronize an external sensor system (e.g., ECG belt system) with marker timing and other programming data from an implantable cardiac device (e.g., a cardiac resynchronization therapy device). Further, the illustrative systems and methods may use marker data (e.g., atrial sensing AS, atrial pacing AP, ventricular sensing VS, ventricular pacing VP, effective capture E, ineffective capture I) to annotate parts of ECG recordings by the external sensor system and to aid in detection and diagnosis. For example, QRS onset detection may be augmented based on VP/VS markers. Further, for example, pacing artifacts may be avoided by blanking or other means for a certain time period (e.g., about 5 milliseconds (ms) to about 10 ms) after delivery of ventricular paces, especially left ventricular paces. Still further, for example, cardiac cycles/events labeled as VS or ineffective pace (I) by the device may be eliminated, or "ruled out," when processing electrical heterogeneity information (e.g., dyssynchrony information) during LV pacing or biventricular pacing.

The illustrative systems and methods could also annotate external sensor data to mark various certain cardiac events such as, e.g., atrial depolarization based on AS/AP markers, ventricular depolarization based on VP, VS markers, difference in timing between an A-event and the next succeeding V event to mark an AV interval, etc. Further, the illustrative systems and methods could combine ECG activity monitored by a plurality of external electrodes with non-ECG sensor data like an external pressure sensor data or an external acoustic sensor data to visualize and calculate timing of device sensing or pacing with respect to timing of certain mechanical events like closing of heart valves or start of ventricular systole, diastole, etc. Still further, the illustrative systems and methods could also synchronize ECG activity monitored by a plurality of external electrodes with data from another implantable device (e.g., waveforms from a left ventricular assist device (LVAD). Then, the illustrative systems and methods may be used to adjust cardiac therapy based on electro-mechanical timings provided by the supplemented ECG activity. For example, pacing parameters may be optimized to shorten the interval between timing of delivery of pacing and start of systole or maximize ejection time (e.g., duration of systole).

One illustrative system for use in cardiac evaluation may include electrode apparatus comprising a plurality of external electrodes to monitor electrical activity from tissue of a patient, a communication interface to receive cardiac information from at least one medical device, and a computing apparatus comprising processing circuitry and operably coupled to the electrode apparatus and the communication interface. The computing apparatus may be configured to monitor electrical activity using the plurality of external electrodes, receive supplemental cardiac data from at least one medical device via the communication interface, and synchronize the monitored electrical activity or data based on the monitored electrical activity to the supplemental cardiac data resulting in synchronized cardiac information.

One illustrative method for use in cardiac evaluation may include monitoring electrical activity from tissue of a patient using a plurality of external electrodes, receiving supplemental cardiac data from at least one medical device, and synchronizing the monitored electrical activity or data based on the monitored electrical activity to the supplemental cardiac data resulting in synchronized cardiac information.

One illustrative system for use in cardiac evaluation may include electrode apparatus comprising a plurality of external electrodes to monitor electrical activity from tissue of a patient, a communication interface to receive cardiac information from at least one medical device, a display comprising a graphical user interface to present information for use in assisting a user in at least one of assessing a patient's cardiac health and evaluating and adjusting cardiac therapy delivered to a patient, and a computing apparatus comprising processing circuitry and operably coupled to the electrode apparatus and the communication interface. The computing apparatus may be configured to monitor electrical activity using the plurality of external electrodes, receive supplemental cardiac data from at least one medical device via the communication interface, synchronize the monitored electrical activity or data based on the monitored electrical activity to the supplemental cardiac data resulting in synchronized cardiac information, and display, on the graphical user interface, at least part of the monitored electrical activity or data based thereon annotated with at least part of the supplemental cardiac data.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
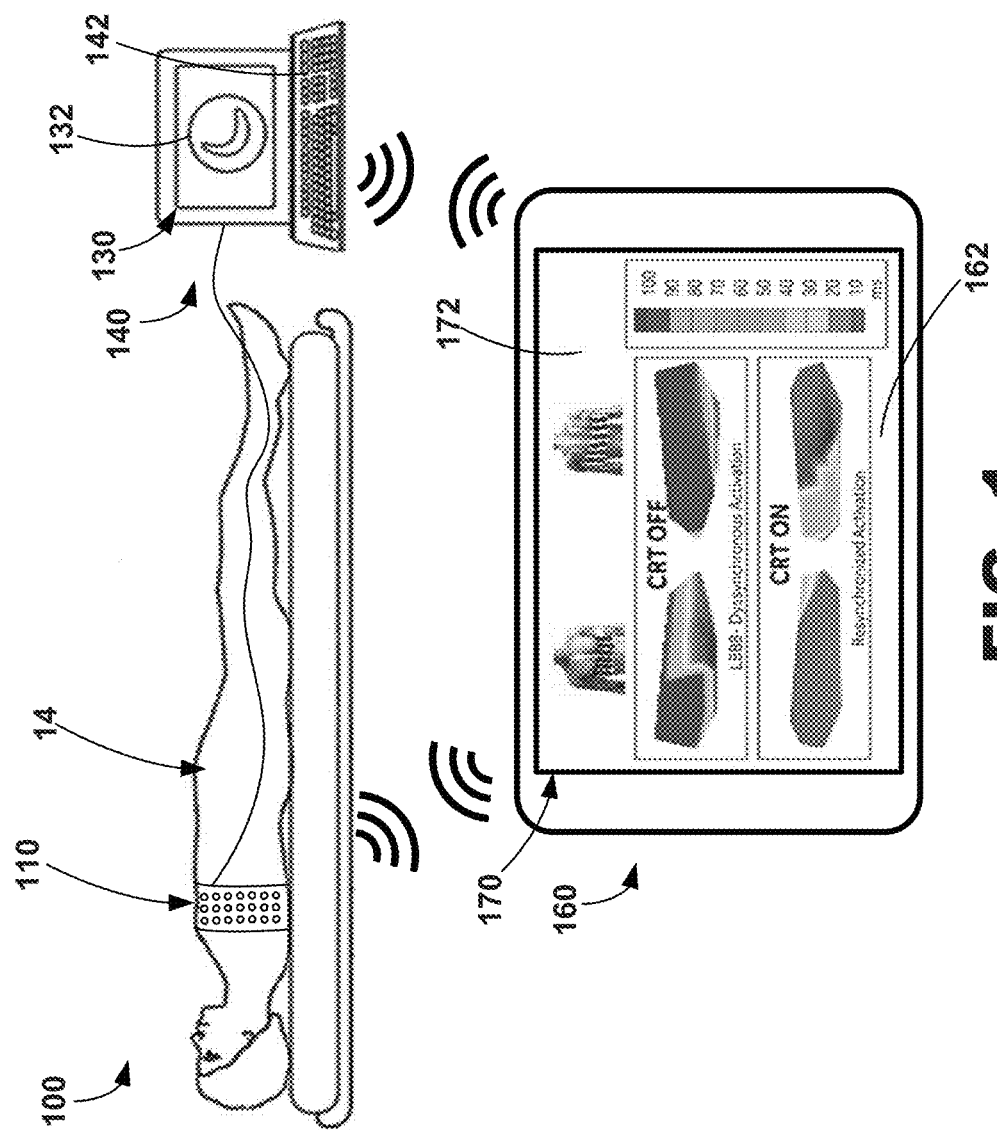
FIG. 1 is a diagram of an illustrative system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and that structural changes may be made without departing from (e.g., still falling within) the scope of the disclosure presented hereby.

Illustrative systems and methods shall be described with reference to FIGS. 1-8. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) signals (e.g., torso-surface potentials) may be measured, or monitored, using a plurality of external electrodes positioned about the surface, or skin, of a patient. The ECG signals may be used to evaluate and configure cardiac therapy such as, e.g., cardiac therapy provide by an implantable medical device performing cardiac resynchronization therapy (CRT). As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to optimize one or more settings, or parameters, of cardiac therapy (e.g., pacing therapy) such as CRT.

Various illustrative systems, methods, and graphical user interfaces may be configured to use electrode apparatus including external electrodes, display apparatus, and computing apparatus to noninvasively assist a user (e.g., a physician) in the evaluation of cardiac health and/or the configuration (e.g., optimization) of cardiac therapy. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to locate, or place, one or more pacing electrodes proximate the patient's heart in conjunction with the configuration of cardiac therapy.

For example, the illustrative systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, pre-excitation intervals such as A-V and V-V intervals, etc. Illustrative systems and methods that use imaging apparatus and/or electrode apparatus may be described in U.S. Pat. App. Pub. No. 2014/0371832 to Ghosh published on Dec. 18, 2014, U.S. Pat. App. Pub. No. 2014/0371833 to Ghosh et al. published on Dec. 18, 2014, U.S. Pat. App. Pub. No. 2014/0323892 to Ghosh et al. published on Oct. 30, 2014, U.S. Pat. App. Pub. No. 2014/0323882 to Ghosh et al. published on Oct. 20, 2014, each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The computing apparatus 140 and the remote computing device 160 may each include display apparatus 130, 160, respectively, that may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the therapeutic nature of one or more parameters related to cardiac therapy such as, e.g., pacing parameters, lead location, etc. More specifically, for example, the QRS complex of a single cardiac cycle may be evaluated for one or more metrics such as, e.g., QRS onset, QRS offset, QRS peak, electrical heterogeneity information (EHI), electrical activation times referenced to the earliest activation time, left ventricular or thoracic standard deviation of electrical activation times (LVED), standard deviation of activation times (SDAT), average left ventricular or thoracic surrogate electrical activation times (LVAT), QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of configuration information related to the cardiac therapy delivered by cardiac therapy apparatus such as, e.g., an implantable medical device.

Each of the remote computing apparatus 160 and computing device 140 may include a communication interface. The communication interfaces of the remote computing apparatus 160 and the computing device 140 may be used to communicate with other devices and apparatus such as the electrode apparatus 110 and each other. As will be described further herein, the communication interfaces may be used to acquire supplemental cardiac data from a plurality of different implanted or external medical devices. In one embodiment, the communication interfaces may include a transceiver and antenna for wirelessly communicating with an external device using radio frequency (RF) communication or other communication protocols. Further, the communication interfaces may be configured to be unidirectional or bi-directional.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or nonvolatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user. Each of the remote computing apparatus 140 and local computing device may include a communication interface. The communication interface of the remote computing apparatus 140 may be referred to as the remote communication interface, and the communication interface of the local computing device 160 may be referred to as the local communication interface. The communication interfaces of the remote computing apparatus 160 and the computing device 140 may be used to communicate with other devices and apparatus such as the electrode apparatus 110, any other medical device that may include supplemental cardiac data, and each other. In one embodiment, the communication interfaces may include a transceiver and antenna for wirelessly communicating with an external device using radio frequency (RF) communication or other communication protocols. Further, the communication interfaces may be configured to be unidirectional or bi-directional.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
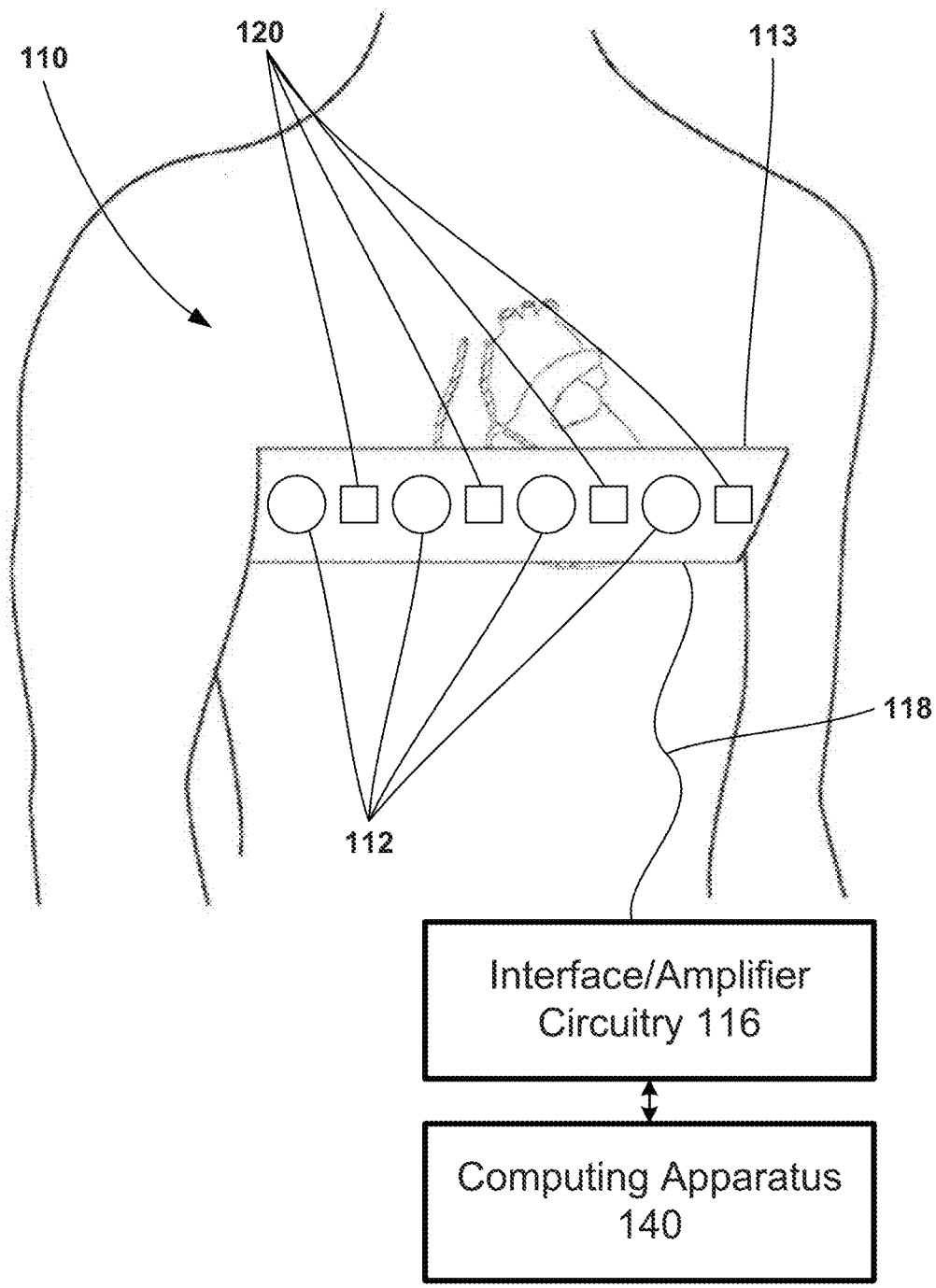
FIGS. 2-3 are diagrams of illustrative external electrode apparatus for measuring torso-surface potentials.

The illustrative electrode apparatus 110 may be configured to measure body-surface potentials of a patient 14 and, more particularly, torso-surface potentials of a patient 14. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

The illustrative electrode apparatus 110 may be further configured to measure, or monitor, sounds from at least one or both the patient 14. As shown in FIG. 2, the illustrative electrode apparatus 110 may include a set, or array, of acoustic sensors 120 attached, or coupled, to the strap 113. The strap 113 may be configured to be wrapped around the torso of a patient 14 such that the acoustic sensors 120 surround the patient's heart. As further illustrated, the acoustic sensors 120 may be positioned around the circumference of a patient 14, including the posterior, lateral, posterolateral, anterolateral, and anterior locations of the torso of a patient 14.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 14. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 14. Still further, in other examples, one or both of the electrodes 112 and the acoustic sensors 120 may be part of, or located within, two sections of material or two patches. One of the two patches may be located on the anterior side of the torso of the patient 14 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 14 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 14 across the left side of the patient 14 to the posterior side of the patient 14. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 14. Instead, the electrodes 112 and acoustic sensors 120 may be arranged in an array that extends only part of the way or partially around the patient 14. For example, the electrodes 112 and acoustic sensors 120 may be distributed on the anterior, posterior, and left sides of the patient with less or no electrodes and acoustic sensors proximate the right side (including posterior and anterior regions of the right side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to provide electrocardiogram (ECG) signals, information, or data from the patient's heart as will be further described herein. The computing apparatus 140 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient.

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with less noise from averaging three caudally located reference signals.

Figure 3:
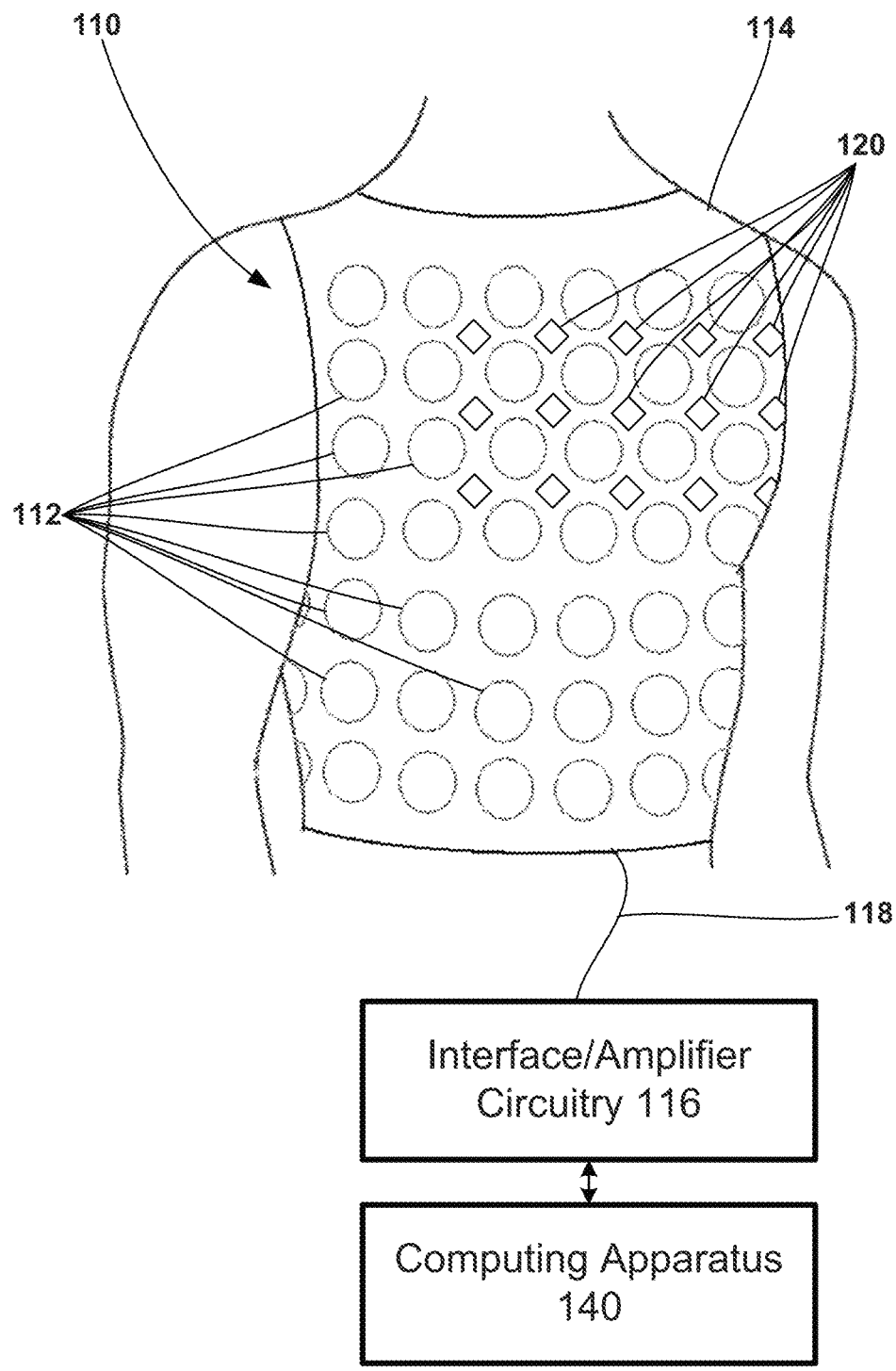

FIG. 3 illustrates another illustrative electrode apparatus 110 that includes a plurality of electrodes 112 configured to surround the heart of the patient 14 and record, or monitor, the electrical signals associated with the depolarization and repolarization of the heart after the signals have propagated through the torso of the patient 14 and a plurality of acoustic sensors 120 configured to surround the heart of the patient 14 and record, or monitor, the sound signals associated with the heart after the signals have propagated through the torso of the patient 14. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 14, including, for example, the posterior, lateral, posterolateral, anterolateral, and anterior locations of the torso of a patient 14.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 14. Further, the vest 114 may be marked to assist in determining the location of the electrodes 112 and the acoustic sensors 120 on the surface of the torso of the patient 14. In some examples, there may be about 25 to about 256 electrodes 112 and about 25 to about 256 acoustic sensors 120 distributed around the torso of the patient 14, though other configurations may have more or fewer electrodes 112 and more or fewer acoustic sensors 120.

Further, it is to be understood that the computing apparatus 140, the remote computing device 160, and any other devices described herein may be operatively coupled to each other in a plurality of different ways so as to perform, or execute, the functionality described herein. For example, in the embodiment depicted, the computing device 140, the remote computing device 160, and another other device or devices that may be provide supplemental cardiac data may be wireless operably coupled to each other as depicted by the wireless signal lines emanating therebetween in FIG. 1. Additionally, as opposed to wireless connections, one or more of the computing apparatus 140, the remoting computing device 160, and other devices providing supplemental cardiac data may be operably coupled to each other through one or wired electrical connections.

The illustrative systems and methods may be used to provide noninvasive assistance to a user in the evaluation of a patient's cardiac health and/or evaluation and configuration of cardiac therapy being presently delivered to the patient (e.g., by an implantable medical device, by a LVAD, etc.). For example, the illustrative systems and methods may be used to assist a user in the configuration and/or adjustment of one or more cardiac therapy settings such as, e.g., optimization of the A-V interval, or delay, of pacing therapy (e.g., left ventricular-only, or left univentricular, pacing therapy) and the A-V interval, or delay, and the V-V interval, or delay, of pacing therapy (e.g., biventricular pacing therapy).

Figure 4:
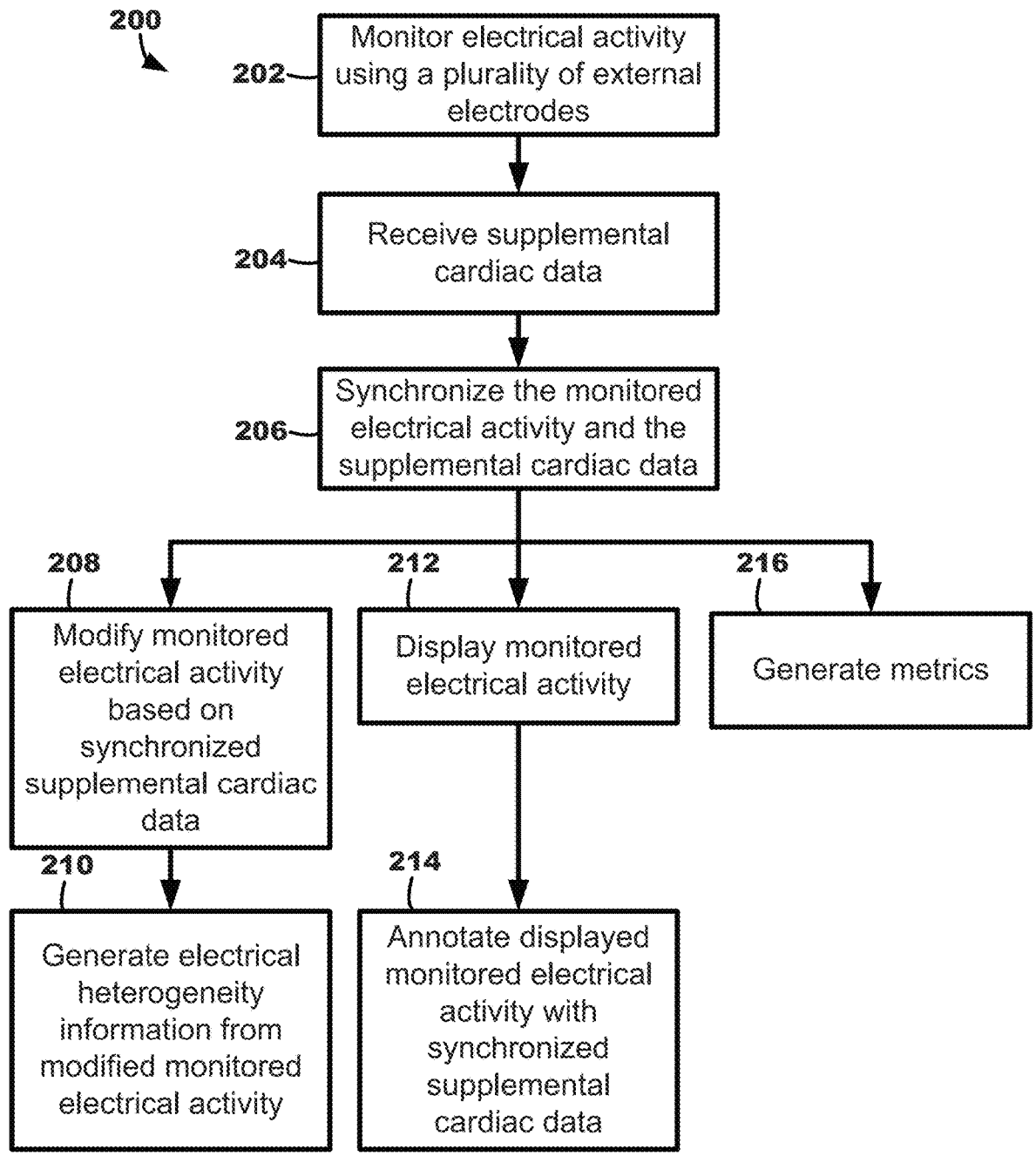
FIG. 4 is a block diagram of an illustrative method of providing synchronized external electrical activity with supplemental cardiac data.

An illustrative method 200 of providing synchronized external electrical activity with supplemental cardiac data is depicted in FIG. 4. The illustrative method 200 may be generally described linking electrical activity monitored by a plurality of external electrodes from the skin of a patient to supplemental cardiac data that is provided by any other device configured to collect cardiac data from the patient.

The illustrative method 200 may include monitoring, or measuring, electrical activity using a plurality of external electrodes 202. The plurality of external electrodes may be similar to the external electrodes provided by the electrode apparatus 110 as described herein with respect to FIGS. 1-3. For example, the plurality of external electrodes may be part, or incorporated into, a vest or band that is located about a patient's torso. More specifically, the plurality of electrodes may be described as being surface electrodes positioned in an array configured to be located proximate the skin of the torso of a patient. The electrical activity monitored during process 202 prior to the delivery of cardiac therapy may be referred to as "baseline" electrical activity because no therapy is delivered to the patient such that the patient's heart is in its natural, or intrinsic, rhythm.

The method 200 may further include receiving supplemental cardiac data 204. The supplemental cardiac data may include any data other than the monitored electrical activity by the plurality of external electrodes that is related to the patient's heart. For example, the supplemental cardiac data may include various signals representative of data over time such as internal cardiac electrical signals (e.g., measured beneath the patient's skin), cardiac sounds, cardiac pressures, blood flows, estimated instantaneous flow waveforms provided by a left ventricular assist device, etc.

Further, for example, the supplemental cardiac data may include various markers indicative of occurrence of cardiac events. More specifically, such markers may include markers indicative an intrinsic atrial depolarization, atrial pace, a premature atrial complex, an intrinsic ventricular depolarization, ventricular pace, a premature ventricular complex, ventricular repolarization during an intrinsic or paced ventricular event, effective ventricular or atrial capture, ineffective ventricular or atrial capture, heart valve closure, heart valve opening, systole, and diastole.

The supplemental cardiac data may be acquired from a plurality of different implanted or external sources. For example, the supplemental cardiac data may be acquired from an implantable medical device. Further, for example, the supplemental cardiac data may be acquired from an external array of acoustic sensors such as shown herein with respect to the electrode apparatus 110 of FIGS. 1-3. Still further, for example, the supplemental cardiac data may be acquired the from a cardiac pacing device, a left ventricular assist device, cardioverter-defibrillator, a subcutaneous monitoring device, and an intracardiac pressure sensor.

Once electrical activity has been monitored 202 and the supplemental cardiac data has been received 204, the method 200 may include synchronizing the monitored electrical activity and the supplemental cardiac data 206. For example, each of the monitored electrical activity and the supplemental cardiac data may have time information (e.g., time stamps) related thereto. In other words, when the monitored electrical activity and the supplemental cardiac data are collected, a clock may "keep track" of the data with respect to time. The time information of the monitored electrical activity and the time information of the supplemental cardiac data may be linked so as to synchronize the monitored electrical activity and the supplemental cardiac data. Further, for example, each of the electrode apparatus/computing apparatus and the device providing the supplemental cardiac data may include clocks that will be synchronized so that when the device sends the marker information along with the clock-cycle or time-stamps measured by the implantable device, the electrode apparatus/computing apparatus can receive and place the marker signal in proper timing with respect to its own clock and own data. Still further, for example, synchronization between the electrode apparatus/computing apparatus and the device providing supplemental cardiac data may be performed by matching the clock-time of apparatus and device to each other or calibrating them to a time server. In at least one embodiment, such synchronization may be performed via cloud-based technologies.

After the monitored electrical activity and the supplemental cardiac data has been synchronized, or linked, the method 200 may utilize such synchronized, or linked, to perform various processes to enhance the monitored electrical activity, to display the synchronized cardiac data, and generate one or more metrics with respect to the synchronized cardiac data.

For example, the method 200 may include modifying monitored electrical activity based on synchronized supplemental cardiac data 208. For instance, the monitored electrical activity using the plurality of external electrodes may be used for further analysis. However, the monitored electrical activity may be negatively affected by various cardiac events such as, e.g., pacing pulses from an implantable pacemaker. As such, in one or more embodiments, monitored electrical activity may be disregarded for a selected period of time following a ventricular pace indicated by the supplemental cardiac data. In this way, the ventricular pace may not negatively affect the monitored electrical activity used for analysis. The selected period of time may between about 1 milliseconds (ms) and 20 ms. In at least embodiment, the selected period of time is 5 ms. The selected period of time may be referred to as a blanking period. In other words, the supplemental cardiac data may be used to filter, or "clean up," the monitored electrical activity.

After the monitored electrical activity has been modified, the method 200 may further generated electrical heterogeneity information (EHI) 210 based on the modified, monitored electrical activity. The EHI may be described as information, or data, representative of at least one of mechanical cardiac functionality and electrical cardiac functionality. The EHI and other cardiac therapy information may be described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety.

Electrical heterogeneity information (e.g., data) may be defined as information indicative of at least one of mechanical synchrony or dyssynchrony of the heart and/or electrical synchrony or dyssynchrony of the heart. In other words, electrical heterogeneity information may represent a surrogate of actual mechanical and/or electrical functionality of a patient's heart. In at least one embodiment, relative changes in electrical heterogeneity information (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). The left ventricular pressure may be typically monitored invasively with a pressure sensor located in the left ventricular of a patient's heart. As such, the use of electrical heterogeneity information to determine a surrogate value representative of the left ventricular pressure may avoid invasive monitoring using a left ventricular pressure sensor.

In at least one embodiment, the electrical heterogeneity information may include a standard deviation of ventricular activation times measured using some or all of the external electrodes, e.g., of the electrode apparatus 110. Further, local, or regional, electrical heterogeneity information may include standard deviations and/or averages of activation times measured using electrodes located in certain anatomic areas of the torso. For example, external electrodes on the left side of the torso of a patient may be used to compute local, or regional, left electrical heterogeneity information.

The electrical heterogeneity information may be generated using one or more various systems and/or methods. For example, electrical heterogeneity information may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

Electrical heterogeneity information may include one or more metrics or indices. For example, one of the metrics, or indices, of electrical heterogeneity may be a standard deviation of activation times (SDAT) measured using some or all of the electrodes on the surface of the torso of a patient. In some examples, the SDAT may be calculated using the estimated cardiac activation times over the surface of a model heart.

Another metric, or index, of electrical heterogeneity may be a left standard deviation of surrogate electrical activation times (LVED) monitored by external electrodes located proximate the left side of a patient. Further, another metric, or index, of electrical heterogeneity may include an average of surrogate electrical activation times (LVAT) monitored by external electrodes located proximate the left side of a patient. The LVED and LVAT may be determined (e.g., calculated, computed, etc.) from electrical activity measured only by electrodes proximate the left side of the patient, which may be referred to as "left" electrodes. The left electrodes may be defined as any surface electrodes located proximate the left ventricle, which includes region to left of the patient's sternum and spine. In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Another illustrative metric, or index, of dyssynchrony may be a range of activation times (RAT) that may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another illustrative metric, or index, of electrical heterogeneity information may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The illustrative metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the electrical heterogeneity information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Heterogeneity information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZAING CRT THERAPY" and published on Apr. 16, 2009, each of which is incorporated herein by reference in its entirety.

Further, the method 200 may include displaying monitored electrical activity 212 and annotating the displayed monitored electrical activity with the synchronized supplemental cardiac data 214. An illustrative graphical user interface 250 depicting monitored external electrical activity 260 annotated with supplemental cardiac data are shown in FIG. 5.

Figure 5:
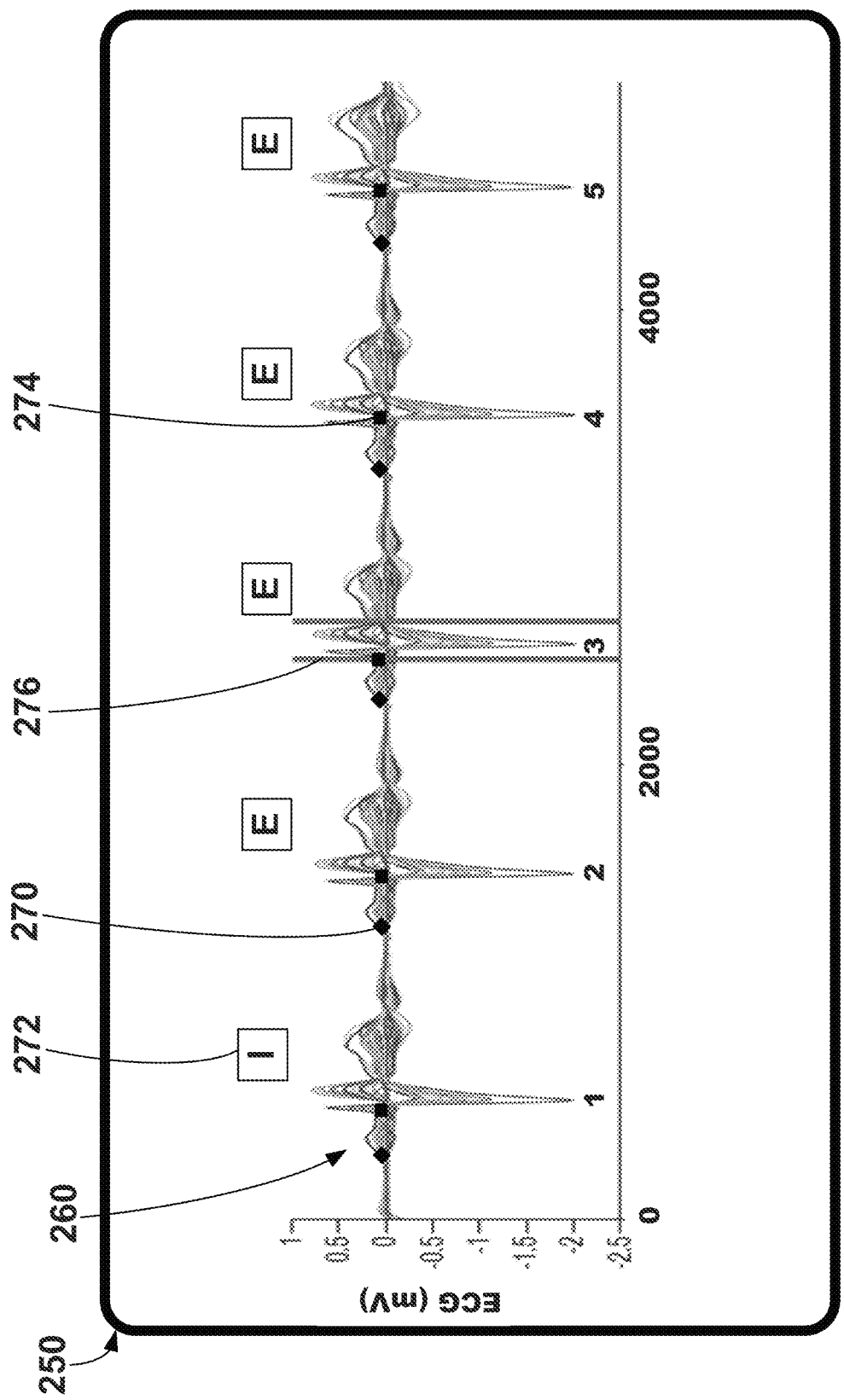
FIG. 5 is an illustrative graphical user interface depicting external electrical activity annotated with supplemental cardiac data.

The graphical user interface 250 of FIG. 5 depicts a plurality of external electrical signals 260 plotted over 5 heart beats or cardiac cycles. A variety of markers from the supplemental cardiac data are annotated about the electrical signals. For example, paced atrial markers 270 (one of which is labeled) indicative of when atrial paces occurred are represented by solid diamonds. Further, for example, ventricular capture indicators 272 (one of which is labeled) are located proximate the electrical signals 260 proximate each cardiac cycle indicating either effective ventricular capture with the letter "E" in a square or ineffective ventricular capture with the letter "I" in a square. Still further, for example, paced ventricle markers 274 (one of which is labeled) indicative of when left ventricular paces occurred are represented by solid squares. And still further, for example, QRS onset and QRS offset indicators 276 (one of which is labeled) indicative of when QRS onset and offset are represented by solid vertical lines.

Although only a few pieces of supplemental cardiac data are annotated on the monitored electrical activity on the graphical user interface 250 shown in FIG. 5, it is be understood that any of the supplemental cardiac described herein may be annotated, or added, to the monitored electrical activity on the graphical user interface 250. Additionally, the illustrative systems and methods described herein may also allow users to manually annotate the monitored electrical activity and any other supplemental cardiac data on the graphical user interface. For example, a user may manually annotate ventricular events on the monitored electrical activity. Further, the illustrative systems and methods may allow configuring various cardiac therapy devices parameters based, at least in part, on the displayed monitored electrical activity, generated EHI, and supplemental cardiac data. In other words, all the tracings and annotations depicted on the graphical user interface may be evaluated to make decisions about final device parameters.

The method 200 may further include generating one or more metrics 216 using data from both of the monitored electrical activity and the supplemental cardiac data. For example, at least one interval between a first event indicated by the monitored electrical activity and a second event indicated by the supplemental cardiac data may be generated. Examples of such intervals may be cross-chamber intervals like intervals between one atrial event and the next ventricular event or intervals between two successive events in the same chamber like, e.g., atrial-to-atrial intervals or ventricular-to-ventricular intervals which provide the lengths of atrial or ventricular cycles.

Figure 6:
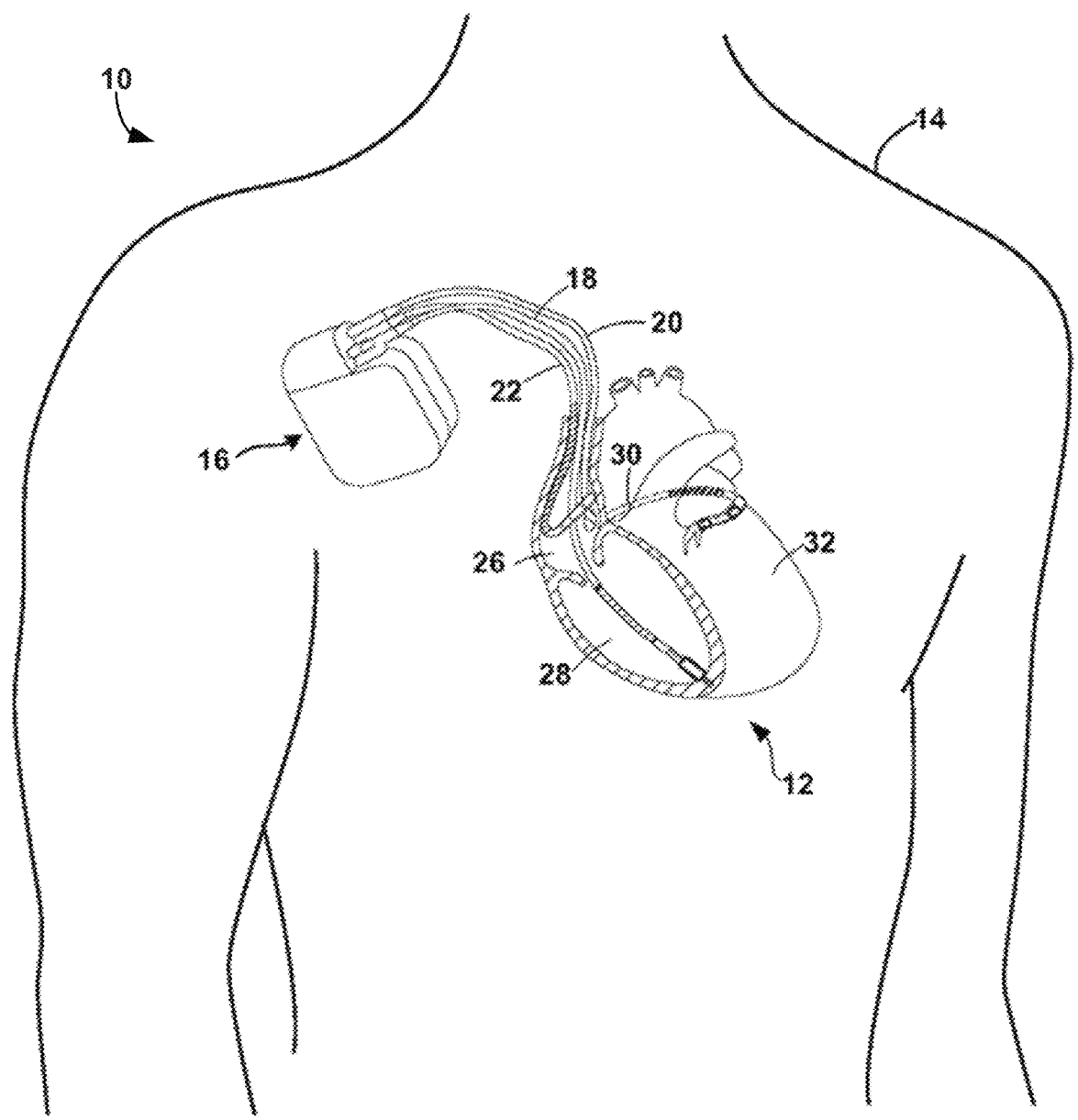
FIG. 6 is a diagram of an illustrative system including an illustrative implantable medical device (IMD).

Illustrative cardiac therapy systems and devices may be further described herein with reference to FIGS. 6-8 that may utilizes the illustrative systems, interfaces, methods, and processes described herein with respect to FIGS. 1-5. For example, the therapy system 10 described in FIGS. 6-8 may be configured to provide supplemental cardiac data to the illustrative systems and methods for use in synchronization with monitored electrical activity.

FIG. 6 is a conceptual diagram illustrating an illustrative therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 6, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the 1 MB. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the 1 MB 16 may detect arrhythmia of the heart 12, such as fibrillation of the ventricles 28, 32, and deliver defibrillation therapy to the heart 12 in the form of electrical pulses. In some examples, 1 MB 16 may be programmed to deliver a progression of therapies, e.g., pulses with increasing energy levels, until a fibrillation of heart 12 is stopped.

Figure 7A:
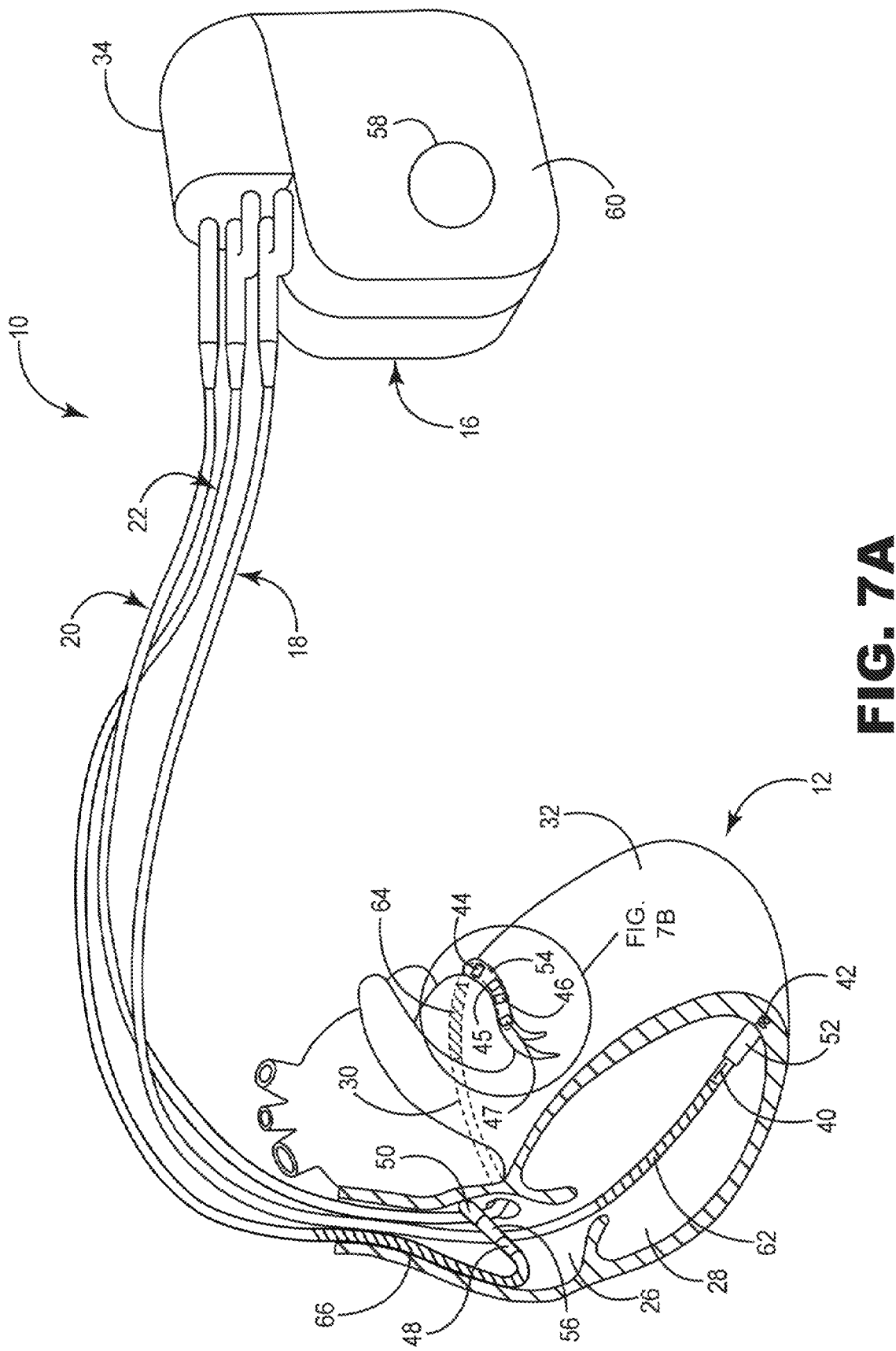
FIG. 7A is a diagram of the illustrative IMD of FIG. 6.
Figure 7B:
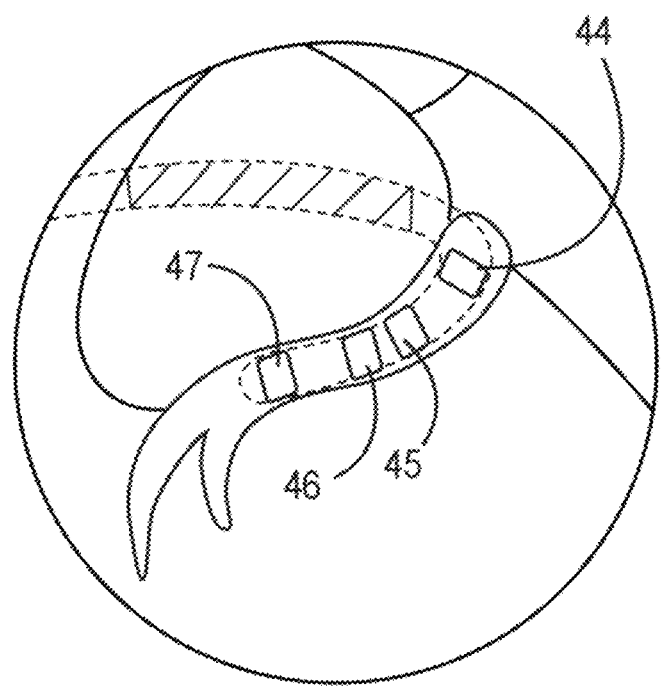
FIG. 7B is a diagram of an enlarged view of a distal end of the electrical lead disposed in the left ventricle of FIG. 7A.

FIGS. 7A-7B are conceptual diagrams illustrating the 1 MB 16 and the leads 18, 20, 22 of therapy system 10 of FIG. 6 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 7A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 7A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 6-8 is merely one example. In other examples, the therapy system may include epicardial leads and/or patch electrodes instead of or in addition to the transvenous leads 18, 20, 22 illustrated in FIG. 6. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 6). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 6-8. Still further, other therapy systems may include a single lead that extends from the IMD 16 into the right atrium 26 or the right ventricle 28, or two leads that extend into a respective one of the right atrium 26 and the right ventricle 28.

Figure 8A:
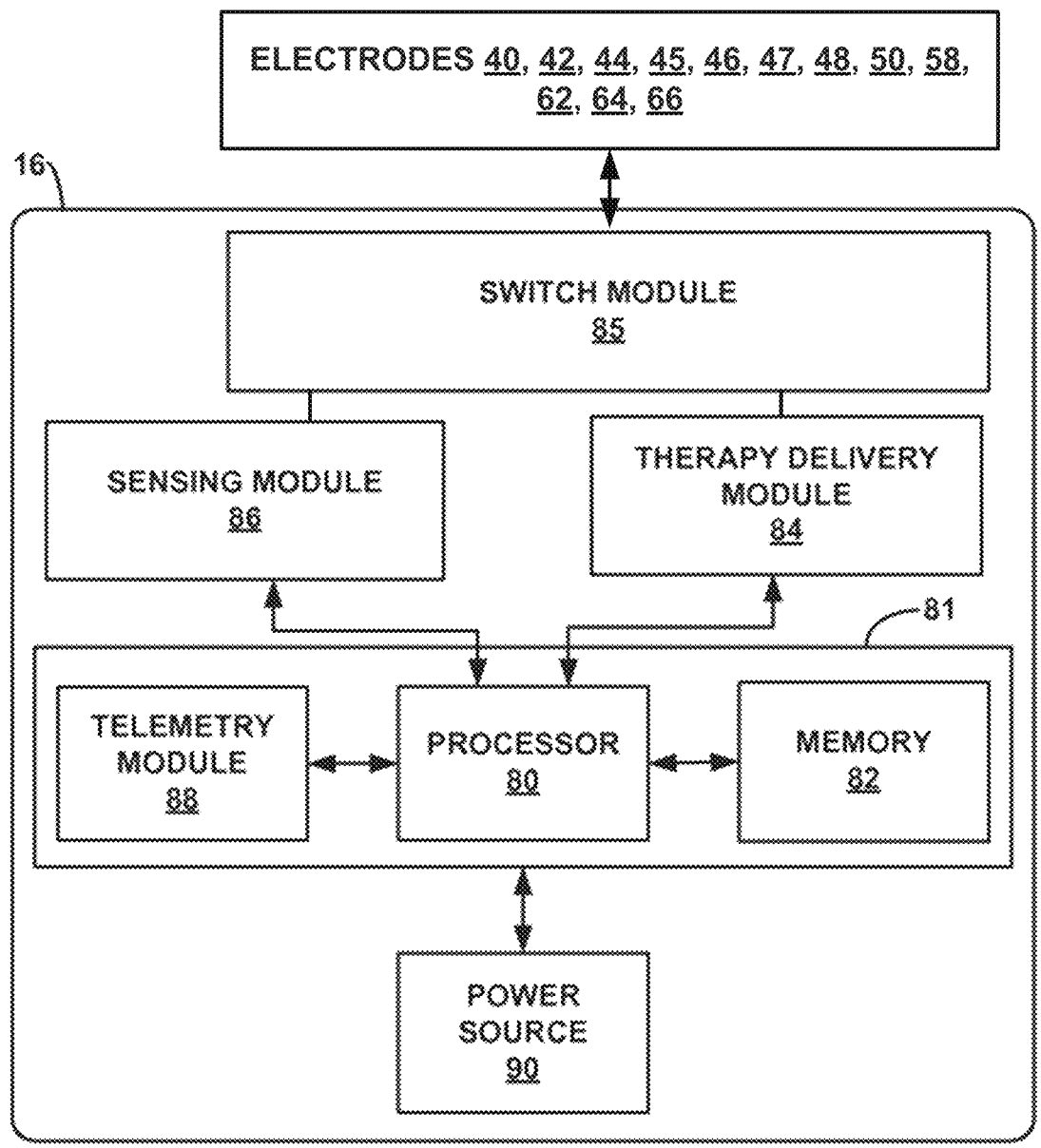
FIG. 8A is a block diagram of an illustrative IMD, e.g., of the systems of FIGS. 6-7.

FIG. 8A is a functional block diagram of one illustrative configuration of the IMD 16. As shown, the IMD 16 may include a control module 81, a therapy delivery module 84 (e.g., which may include a stimulation generator), a sensing module 86, and a power source 90.

The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EE-PROM), flash memory, and/or any other digital media. An illustrative capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 8B:
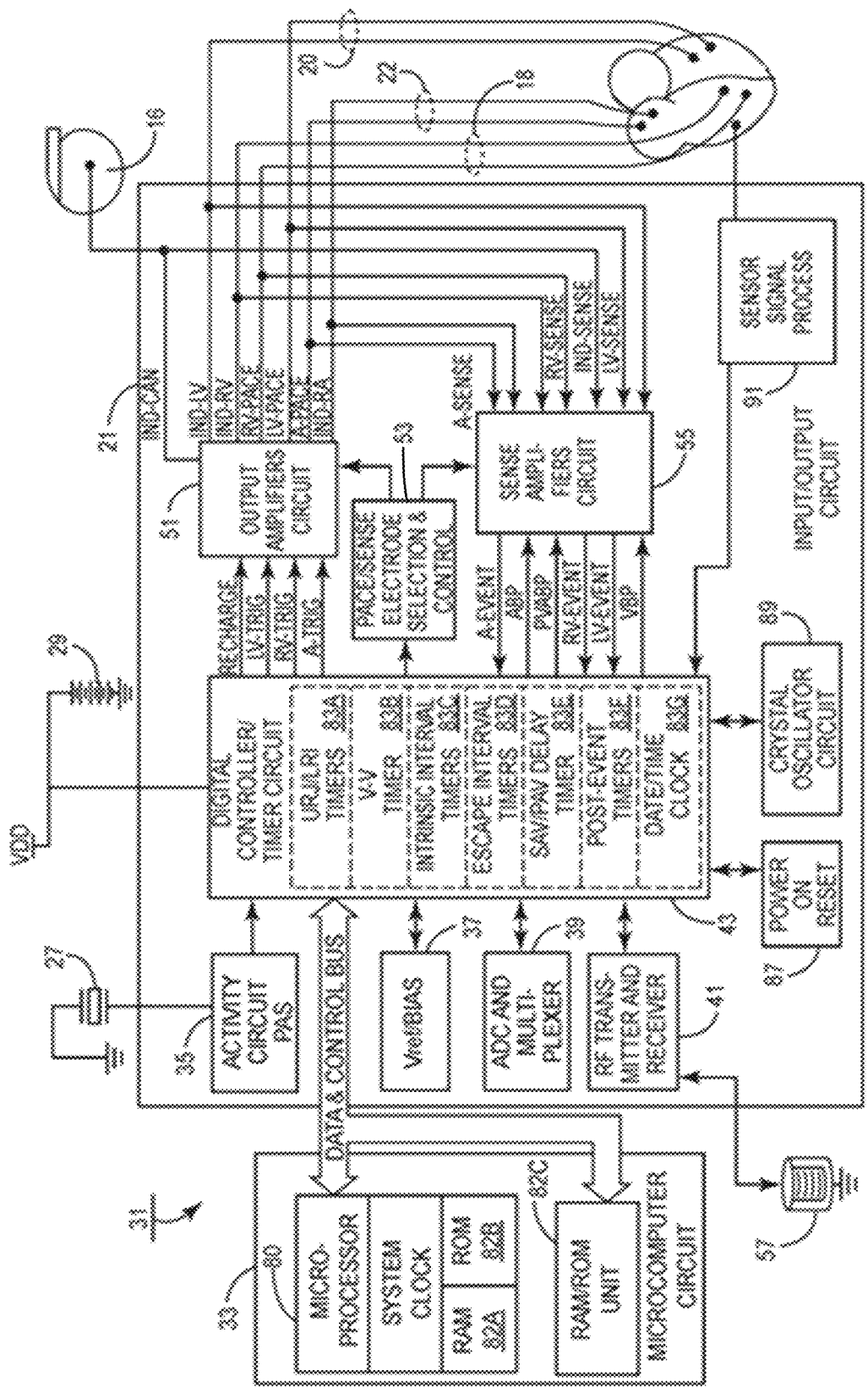
FIG. 8B is another block diagram of an illustrative IMD (e.g., an implantable pulse generator) circuitry and associated leads employed in the systems of FIGS. 6-7.

FIG. 8B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a biventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the illustrative systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, V-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by A-V delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

Embodiment 1: A system for use in cardiac evaluation comprising:
electrode apparatus comprising a plurality of external electrodes to monitor electrical activity from tissue of a patient;
communication interface to receive cardiac information from at least one medical device; and
a computing apparatus comprising processing circuitry and operably coupled to the electrode apparatus and the communication interface, the computing apparatus configured to:
monitor electrical activity using the plurality of external electrodes,
receive supplemental cardiac data from at least one medical device via the communication interface, and
synchronize the monitored electrical activity or data based on the monitored electrical activity to the supplemental cardiac data resulting in synchronized cardiac information.

Embodiment 2: A method for use in cardiac evaluation comprising:
monitoring electrical activity from tissue of a patient using a plurality of external electrodes;
receiving supplemental cardiac data from at least one medical device; and
synchronizing the monitored electrical activity or data based on the monitored electrical activity to the supplemental cardiac data resulting in synchronized cardiac information.

Embodiment 3: The system or method as set forth in any one of embodiments 1-2, wherein the supplemental cardiac data comprises one or more markers indicative of the occurrence of cardiac events.

Embodiment 4: The system or method as set forth in embodiment 3, wherein the one or more markers comprise one or more markers indicative an intrinsic atrial depolarization, atrial pace, a premature atrial complex, an intrinsic ventricular depolarization, ventricular pace, a premature ventricular complex, ventricular repolarization during an intrinsic or paced ventricular event, effective ventricular or atrial capture, ineffective ventricular or atrial capture, heart valve closure, heart valve opening, systole, and diastole Embodiment 5: The system or method as set forth in any one of embodiments 1-4, wherein the supplemental cardiac data is representative of at least one of cardiac electrical signals, cardiac sounds, cardiac pressures, blood flow, and an estimated instantaneous flow waveform provided by a left ventricular assist device.

Embodiment 6: The system or method as set forth in any one of embodiments 1-5, wherein the system further comprises a display comprising a graphical user interface to present information for use in assisting a user in at least one of assessing a patient's cardiac health, evaluating and adjusting cardiac therapy delivered to a patient, and navigating at least one implantable electrode to a region of the patient's heart, wherein the computing apparatus operably coupled to the display and further configured to execute or the method further comprises displaying, on a graphical user interface, at least part of the monitored electrical activity or data based thereon annotated with at least part of the supplemental cardiac data.

Embodiment 7: The system or method as set forth in any one of embodiments 1-6, wherein the computing apparatus is further configured to execute or the method further comprises determining at least one interval between a first event indicated by the monitored electrical activity and a second event indicated by the supplemental cardiac data.

Embodiment 8: The system or method as set forth in any one of embodiments 1-7, wherein the computing apparatus is further configured to execute or the method further comprises modifying the monitored electrical activity based on the supplemental cardiac data.

Embodiment 9: The system or method as set forth in embodiment 8, wherein modifying the monitored electrical activity based on the supplemental cardiac data comprises disregarding the monitored electrical activity for a selected period of time following a ventricular pace indicated by the supplemental cardiac data.

Embodiment 10: The system or method as set forth in any one of embodiments 1-9, wherein the at least one medical device comprises an implantable medical device.

Embodiment 11: The system or method as set forth in any one of embodiments 1-10, wherein the at least one medical device comprises at least one of a cardiac pacing device, a left ventricular assist device, cardioverter-defibrillator, a subcutaneous monitoring device, and an intracardiac pressure sensor.

Embodiment 12: A system for use in cardiac evaluation comprising:
electrode apparatus comprising a plurality of external electrodes to monitor electrical activity from tissue of a patient;
communication interface to receive cardiac information from at least one medical device;
a display comprising a graphical user interface to present information for use in assisting a user in at least one of assessing a patient's cardiac health and evaluating and adjusting cardiac therapy delivered to a patient, and
a computing apparatus comprising processing circuitry and operably coupled to the electrode apparatus and the communication interface, the computing apparatus configured to:
monitor electrical activity using the plurality of external electrodes,
receive supplemental cardiac data from at least one medical device via the communication interface,
synchronize the monitored electrical activity or data based on the monitored electrical activity to the supplemental cardiac data resulting in synchronized cardiac information, and
display, on the graphical user interface, at least part of the monitored electrical activity or data based thereon annotated with at least part of the supplemental cardiac data.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:
1. A system for use in cardiac evaluation comprising:
electrode apparatus comprising a plurality of external electrodes to monitor electrical activity from tissue of a patient;
communication interface to receive supplemental cardiac data from at least one medical device; and a computing apparatus comprising processing circuitry and operably coupled to the electrode apparatus and the communication interface, the computing apparatus configured to:
- monitor electrical activity using the plurality of external electrodes,
- receive supplemental cardiac data from at least one medical device via the communication interface,
- synchronize the monitored electrical activity or data based on the monitored electrical activity to the supplemental cardiac data resulting in synchronized supplemental cardiac data,
- modify the monitored electrical activity based on the synchronized supplemental cardiac data, and
- generate electrical heterogeneity information (EHI) based on the modified monitored electrical activity, wherein the EHI is information or data representative of at least one of mechanical cardiac functionality and electrical cardiac functionality.

2. The system of claim 1, wherein the supplemental cardiac data comprises one or more markers indicative of the occurrence of cardiac events.

3. The system of claim 2, wherein the one or more markers comprise one or more markers indicative an intrinsic atrial depolarization, atrial pace, a premature atrial complex, an intrinsic ventricular depolarization, ventricular pace, a premature ventricular complex, ventricular repolarization during an intrinsic or paced ventricular event, effective ventricular or atrial capture, ineffective ventricular or atrial capture, heart valve closure, heart valve opening, systole, and diastole.

4. The system of claim 1, wherein the supplemental cardiac data is representative of at least one of cardiac electrical signals, cardiac sounds, cardiac pressures, blood flow, and an estimated instantaneous flow waveform provided by a left ventricular assist device.

5. The system of claim 1, the system further comprising a display comprising a graphical user interface to present information for use in assisting a user in at least one of assessing a patient's cardiac health, evaluating and adjusting cardiac therapy delivered to a patient, and navigating at least one implantable electrode to a region of the patient's heart, wherein the computing apparatus is operably coupled to the display and further configured to:
- display, on the graphical user interface, at least part of the monitored electrical activity or data based thereon annotated with at least part of the synchronized supplemental cardiac data.

6. The system of claim 5, wherein the annotation comprises displaying at least one of a paced atrial marker, a paced left ventricular marker, and an effective or ineffective ventricular capture marker.

7. The system of claim 1, wherein the computing apparatus is further configured to determine at least one interval between a first event indicated by the monitored electrical activity and a second event indicated by the synchronized supplemental cardiac data.

8. The system of claim 1, wherein modifying the monitored electrical activity based on the synchronized supplemental cardiac data comprises disregarding the monitored electrical activity for a selected period of time following a ventricular pace indicated by the synchronized supplemental cardiac data.

9. The system of claim 1, wherein the at least one medical device comprises an implantable medical device.

10. The system of claim 1, wherein the at least one medical device comprises at least one of a cardiac pacing device, a left ventricular assist device, cardioverter-defibrillator, a subcutaneous monitoring device, and an intracardiac pressure sensor.

11. A method for use in cardiac evaluation comprising:
- monitoring electrical activity from tissue of a patient using a plurality of external electrodes;
- receiving supplemental cardiac data from at least one medical device;
- synchronizing the monitored electrical activity or data based on the monitored electrical activity to the supplemental cardiac data resulting in synchronized supplemental cardiac data;
- modifying the monitored electrical activity based on the synchronized supplemental cardiac data; and
- generating electrical heterogeneity information (EHI) based on the modified monitored electrical activity, wherein the EHI is information or data representative of at least one of mechanical cardiac functionality and electrical cardiac functionality.

12. The method of claim 11, wherein the supplemental cardiac data comprises one or more markers indicative of the occurrence of cardiac events.

13. The method of claim 12, wherein the one or more markers comprise one or more markers indicative an intrinsic atrial depolarization, atrial pace, a premature atrial complex, an intrinsic ventricular depolarization, ventricular pace, a premature ventricular complex, ventricular repolarization during an intrinsic or paced ventricular event, effective ventricular or atrial capture, ineffective ventricular or atrial capture, heart valve closure, heart valve opening, systole, and diastole.

14. The method of claim 11, wherein the supplemental cardiac data is representative of at least one of cardiac electrical signals, cardiac sounds, cardiac pressures, blood flow, and an estimated instantaneous flow waveform provided by a left ventricular assist device.

15. The method of claim 11, the method further comprising
- displaying, on a graphical user interface, at least part of the monitored electrical activity or data based thereon annotated with at least part of the synchronized supplemental cardiac data.

16. The method of claim 15, wherein the annotation comprises displaying at least one of a paced atrial marker, a paced left ventricular marker, and an effective or ineffective ventricular capture marker.

17. The method of claim 11, the method further comprising determining at least one interval between a first event indicated by the monitored electrical activity and a second event indicated by the synchronized supplemental cardiac data.

18. The method of claim 11, wherein modifying the monitored electrical activity based on the synchronized supplemental cardiac data comprises disregarding the monitored electrical activity for a selected period of time following a ventricular pace indicated by the synchronized supplemental cardiac data.

19. The method of claim 11, wherein the at least one medical device comprises an implantable medical device.

20. The method of claim 11, wherein the at least one medical device comprises at least one of a cardiac pacing device, a left ventricular assist device, cardioverter-defibrillator, a subcutaneous monitoring device, and an intracardiac pressure sensor.

21. A system for use in cardiac evaluation comprising:
electrode apparatus comprising a plurality of external electrodes to monitor electrical activity from tissue of a patient;
communication interface to receive supplemental cardiac data from at least one medical device;
a display comprising a graphical user interface to present information for use in assisting a user in at least one of assessing a patient's cardiac health and evaluating and adjusting cardiac therapy delivered to a patient, and
a computing apparatus comprising processing circuitry and operably coupled to the electrode apparatus and the communication interface, the computing apparatus configured to:
monitor electrical activity using the plurality of external electrodes,
receive supplemental cardiac data from at least one medical device via the communication interface,
synchronize the monitored electrical activity or data based on the monitored electrical activity to the supplemental cardiac data resulting in synchronized supplemental cardiac data,
modify the monitored electrical activity based on the synchronized supplemental cardiac data, and
generate electrical heterogeneity information (EHI) based on the modified monitored electrical activity, wherein the EHI is information or data representative of at least one of mechanical cardiac functionality and electrical cardiac functionality, and
display, on the graphical user interface, at least part of the monitored electrical activity or data based thereon annotated with at least part of the synchronized supplemental cardiac data.

* * * * *